United States Patent [19]

Marshall

[11] 4,144,645
[45] Mar. 20, 1979

[54] METHOD FOR PREPARATION OF DENTAL CROWNS AND BRIDGES

[75] Inventor: Kenneth H. Marshall, Castlecrag, Australia

[73] Assignee: Premach Pty. Limited, Sydney, Australia

[21] Appl. No.: 744,464

[22] Filed: Nov. 24, 1976

[30] Foreign Application Priority Data

Nov. 28, 1975 [AU] Australia ............................. PC4102

[51] Int. Cl.² ................................................. A61C 5/10
[52] U.S. Cl. .......................................... 32/42; 32/49
[58] Field of Search ......................... 32/49, 42, 27, 40

[56] References Cited

U.S. PATENT DOCUMENTS

| 383,367 | 5/1888 | Patrick | 32/49 |
|---|---|---|---|
| 472,004 | 3/1892 | Sweet et al. | 32/49 |
| 1,157,681 | 10/1915 | Dalbey | 32/49 |
| 3,445,935 | 5/1969 | Marshall | 32/40 R |
| 3,600,810 | 8/1971 | Marshall | 32/49 |

Primary Examiner—Russell R. Kinsey
Assistant Examiner—John J. Wilson
Attorney, Agent, or Firm—Finnegan, Henderson, Farabow & Garrett

[57] ABSTRACT

A method for dentists in the preparation of a patient's tooth for a jacket crown, or for bridgework. It involves the use of a block for firm attachment to the cusp of the tooth, said block having prepared side and end surfaces for guiding a dental handpiece in two parameters.

6 Claims, 6 Drawing Figures

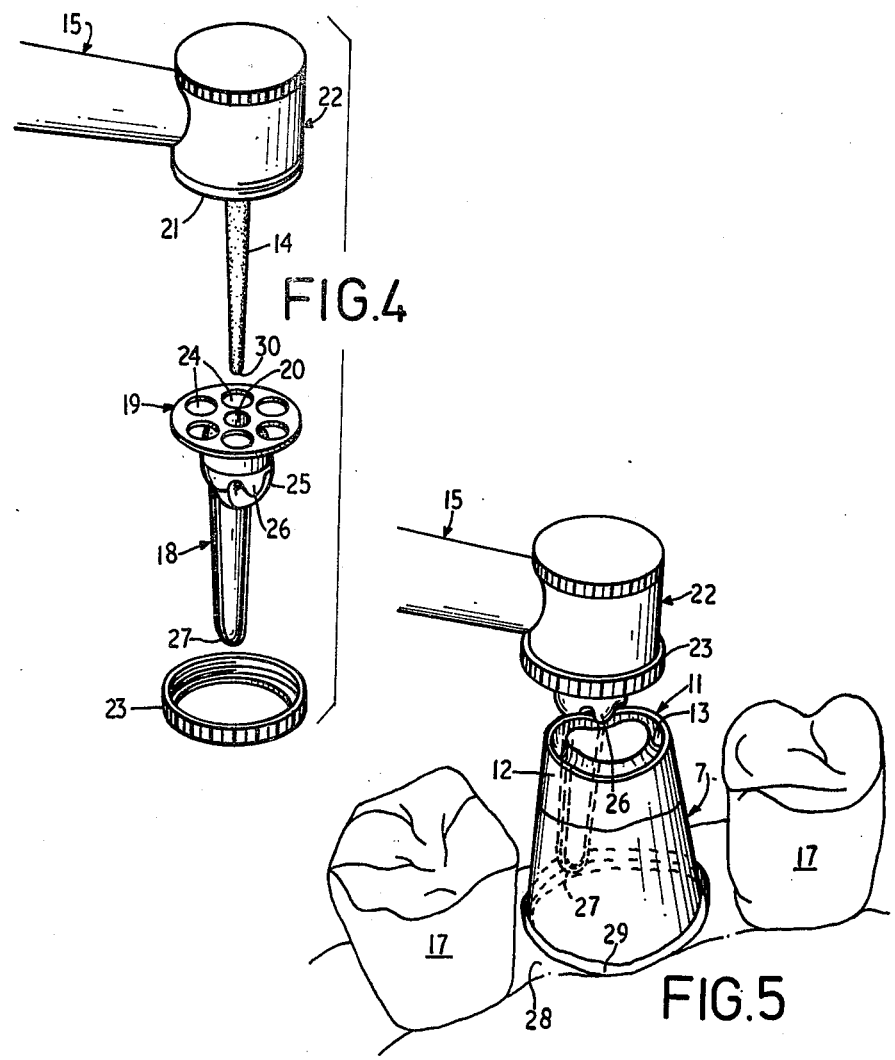
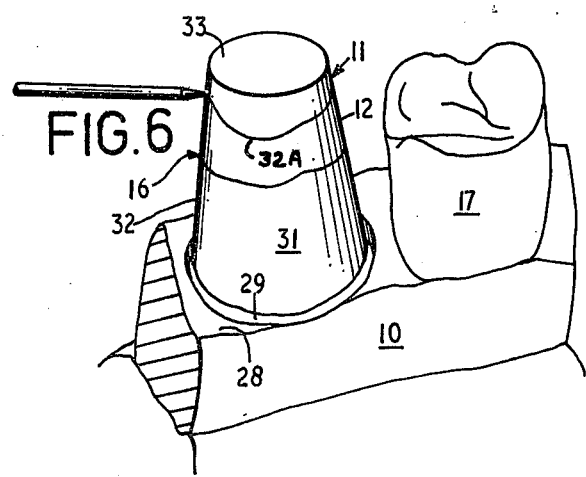

METHOD FOR PREPARATION OF DENTAL CROWNS AND BRIDGES

This invention relates to the utilization of dental aids in the preparation of natural teeth for the fitting of dental crowns and bridges.

Dental aids, such as that which is the subject of U.S. Pat. No. 3,600,810, have already been provided to assist a dental surgeon for more precise and controlled reduction of tooth structure for the provision of a spigot for the fitting of a jacket crown or a dental bridge. These mechanical aids are most effective but can comfortably only be applied to the anterior teeth. When preparation of posterior teeth is required reduction is usually performed freehand by the surgeon due to the limited working space within the patient's mouth.

It is the main object of this invention to assist a dental surgeon in the preparation of a natural tooth for the fitting of a dental crown or bridge while utilizing a so-called contra-angle handpiece. By the invention it is possible to control tooth reduction to achieve predetermined parameters of said preparation.

Another object is to provide a method to be followed by a dental surgeon in tooth reduction which utilizes disposable guide means individually prepared for that tooth for guiding movement of a cutting burr.

It is a further object to provide a method for producing individually prepared guide means to assist the dental surgeon during tooth reduction in two parameters.

According to a feature of the invention there is provided a method of preparing a natural tooth for the fitting of a dental crown or bridge with the use of a rotatable cutting burr supported in a handpiece, comprising fastening to the cusp of the tooth a pre-prepared block having two guide surfaces, attaching to the handpiece a shading guide co-extensive with, and rotatable about, the cutting burr and having a part extending beyond the tip of said cutting burr for engagement sub-gingivally with said tooth, and operating said handpiece to effect reduction of the tooth structure to achieve parameters determined by said guiding surfaces and said extending part of the shading guide.

According to another feature the invention also provides a dental handpiece for use with the above method and comprising a socket connected with an internal driving motor for the mounting of a cutting burr, and a shading guide assembly comprising a stem with a base portion encircling a root end portion of the burr and co-extensive with the burr and having a tip protruding beyond the end of the burr, a pair of oppositely directed abutment arms connected to the stem to partly enclose said tooth and through contact therewith to control rotation of said stem about said burr and an attaching portion connected to the stem for engagement with the handpiece to retain said shading guide rotatably thereon.

According to a further feature of the invention there is provided a method of producing a guide block for use with the above method, and comprising producing a cast of the patient's tooth to obtain by the use of a dental surveyor a model of the intended preparation, temporarily attaching to the cusp of the preparation a block of material, preparing a side wall of said block by the use of a cutting burr with the occlusal area of the preparation serving as a guide, forming an upper surface on said block which is parallel to a sub-gingival shoulder of the preparation, and removing the block from the model.

A preferred embodiment of the invention is illustrated in the accompanying drawings, in which:

FIG. 4 is an exploded perspective view showing the component parts of the handpiece and cutting burr of FIG. 3;

FIG. 5 is a perspective view showing the handpiece and cutting burr in use to produce the required conical contour on the patient's tooth; and, FIG. 6 is a perspective view of a preliminary stage in which an impression of the patient's tooth with the acrylic guide block is being marked by a scriber.

Figure 1:
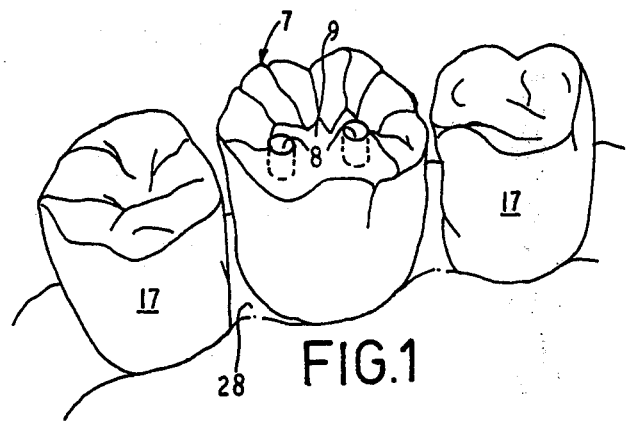
FIG. 1 is a perspective view of some of a patient's teeth showing holes drilled in the cusp of a tooth requiring reduction.
Figure 2:
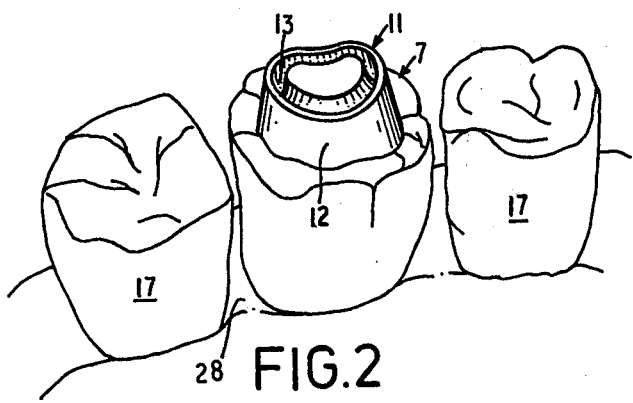
FIG. 2 shows a similar view to FIG. 1 with an acrylic guide block secured to a tooth.
Figure 3:
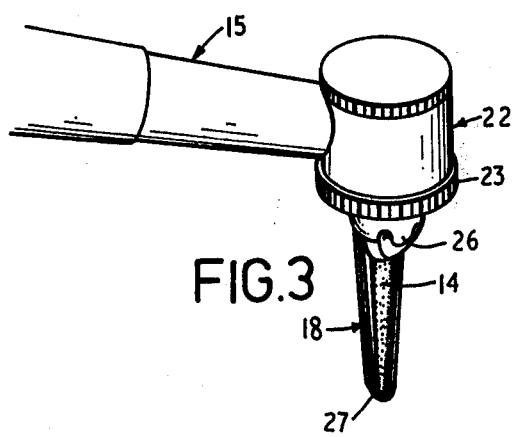
FIG. 3 is a perspective view of a specialized handpiece and cutting burr.

The preferred embodiment of the invention illustrated in the drawings will now be described wherein the method employed by a dental surgeon for the preparation of a natural tooth 7 for the fitting of a dental crown or bridge (not shown) consists of the following steps. Firstly, forming suitable key means, such as a pair of holes 8, see FIG. 1, in the cusp 9 of the patient's tooth and making an impression of the patient's tooth 7 in the respective jaw or part thereof for preparation of a cast 10, FIG. 6, by conventional means. Subsequently, a guide block 11 of acrylic, or other suitable material, will be produced and provided by a dental mechanic in a manner to be described hereafter, and this block 11 will be rigidly secured on the cusp 9 of the patient's tooth 7 and keyed thereto, with (or without) the use of an adhesive. The acrylic block 11 will have a side wall 12 and a top surface track 13 which will serve to guide the surgeon's cutting burr 14 mounted in a handpiece 15 whereby the same preparation of the tooth 16, see FIG. 6, created by the dental mechanic upon the cast 10 will be reproduced on the patient's tooth 7. This will greatly assist the surgeon in his work and reduce considerably the degree of necessary skill, while enabling a precise relationship of axes between several of the patient's teeth 17 required to be prepared for the fitting of dental bridges.

Access by the surgeon to posterior teeth for preparation will be relatively unhindered as all reduction work will be obtained through the use of a contra-angle handpiece 15 with cutting burr 14 having similar overall physical dimensions as a conventional handpiece of this As best seen in FIG. 4, it will include a metal shading guide 18 secured to a circular disc 19 having a medial bore 20 which is large enough to permit the burr 14 to pass therethrough freely and to be partially enclosed by the shroud, or shading guide, 18. The disc 19 is normally located against the underside 21 of the handpiece barrel 22 by means of a ring nut 23. The nut 23 is threadably engaged with the barrel 22 so that the disc 19 and shading guide 18 are free to rotate but not to move axially with respect to the barrel 22.

The disc 19 is provided with large perforations 24 so that exhaust air from the motor within the barrel 22, and also cooling water, can escape therethrough. An enlarged boss 25 is formed integrally with the underside of the disc 19 and one side of said boss is ground so as to form a downwardly directed tongue 26.

When the handpiece 15 is presented to the tooth 7 as shown in FIG. 5, the tongue engages the track 13 in the top of the acrylic block 11 attached to said tooth so that when the burr 14 is moved around the occlusal area of the tooth 7 the shading guide 18 is caused to rotate to maintain concealment of the side of the burr 14 furthest from the tooth 7. In this way inter-proximal reduction is achieved without damage to neighbouring teeth 17 while the end of the curled tip 27 of the guide 18 is always directed towards the axis of the tooth 7 being prepared. It will be seen, therefore, that the boss 25 with its tongue 26 functions as a follower to both guiding surfaces. The tip portion 27 of the guide 18 separates the gingiva 28 from the tooth 7 without damage and allows a sub-gingival groove 29 to be cut due to it extending beyond the end of the burr 14. It will always be engaged with a portion of the tooth 7 which will not be cut and therefore functions as a guide controlling the depth of reduction performed by the outer end portion of the burr 14.

Preferably, the cutting burr 14 used will be of a kind with its cutting face extending from its outer end 30 to a point short of its mounting chuck or barrel 22. The dental surgeon, therefore, will apply the cutting burr 14 to the patient's tooth 7 as shown in FIG. 5 in any one of several ways which will be purely a matter of choice providing that in completing the preparation the tip 27 of the guide 18 is beneath the gingival margin 28 and in contact with the tooth 7 and the handpiece boss 25 is in contact with both the upper guiding track 13 and the outer wall 12 of the acrylic block 11 to ensure control of tooth reduction in two parameters. After completion of the preparation the acrylic block 11 may be severed from the tooth 7 for completion of the preparation.

The acrylic block 11 referred to above is preferably produced by the dental mechanic as follows. The cast 10 of the patient's teeth is made from the impression provided by the surgeon and by the use of a dental surveyor (not shown) onto which is mounted a cutting burr and guide similar to that to be used subsequently by the surgeon, the cast 10 of the tooth 7 for treatment is reduced to a completed preparation 31 considered by the mechanic to be ideal. A block of acrylic 11, in a rough mass is temporarily secured to the cusp of the tooth preparation 31 and by the use of a special burr, i.e. one in which the outer end portion is non-abrasive, the outer wall of the block is reduced as shown in FIG. 6 until the end portion of the burr contacts the wall 32 of the tooth preparation 31, and on the outer wall is scribed a peripheral line 32A parallel to the sub-gingival shoulder 29 on the preparation 31. This can be readily effected by any suitable paralleling means engageable with the shoulder 29. The upper portion 33 of the block 11 above the scribed line 32A is then removed to provide the guiding track 13 at that end of the block 11 which will subsequently serve to limit the axial penetration of the burr 14 beneath the gingiva 28 to produce the sub-gingival shoulder 29 on the patient's tooth 7 (FIG. 5).

A preferred embodiment has been described in the foregoing passages but it should be appreciated that other forms and embodiments are possible within the scope of this invention.

What I claim is:

1. A method of preparing a natural tooth for the fitting of a dental crown or bridge with the use of a rotatable cutting burr supported in a handpiece and having a shading guide coextensive with, and rotatable about, said cutting burr and extending beyond the tip of said cutting burr for engagement sub-gingivally with said tooth, wherein the steps comprise fastening a block by its base, to the cusp of said tooth, said block having three pre-prepared external surfaces, a first one of said surfaces constituting said base, a second one of said surfaces being at an opposite part of said block to said base, and a third one of said surfaces being an external wall joining said first and said second surfaces; and operating said handpiece to effect progressive free-hand reduction of the tooth structure of said natural tooth until said handpiece abuts both of said second and third surfaces simultaneously with said extending part of said shading guide in contact with a sub-gingival part of said tooth thereby to provide controlled limits of said reduction.

2. The method of claim 1 comprising, before fastening of said block to said tooth, the further steps of forming means in said tooth to key said block thereto, and thereafter making an impression of the patient's jaw including at least said tooth.

3. The method of claim 1, wherein in operating said handpiece the part of said handpiece abutting said second and third surfaces is a follower fixed to said shading guide and rotatable about the axis of said cutting burr.

4. A method of producing a guide block for use in preparing a natural tooth for the fitting of a dental crown or bridge, wherein the steps comprise producing a cast from an impression of the natural tooth, creating on said cast with the use of a dental surveyor a model of the intended preparation of the natural tooth which includes a sub-gingival shoulder, temporarily attaching to the cusp of the model tooth so formed a mass of material having bottom and top surfaces and an outer face, so that said bottom surface contains an impression of the configuration of said cusp, preparing said outer face of said mass to form a side wall surface with the occlusal area of the model tooth serving as a guide, and forming said top surface on said mass corresponding contoured and parallel to a predetermined sub-gingival shoulder of the model tooth, thereby creating from said mass a block having three prepared external surfaces of which two serve as controlling limits on free-hand reduction of the natural tooth by a dental surgeon, and thence removing said block from said model tooth for supply as an aid to the dental surgeon.

5. The method of claim 4, wherein the step of preparing said side wall surface of said mass includes cutting with a cutting burr until a part of said burr maintains contact with said occlusal area of the model tooth during a full rotation of said burr around said model tooth.

6. The method of claim 4, wherein the step of forming said outer end surface on said mass includes scribing around said side wall surface of said mass a line which is parallel to said sub-gingival shoulder, cutting off the outer end of said mass beyond said line, and forming a recess in the top of said block so formed.

* * * * *